United States Patent [19]

Mills et al.

[11] 4,202,344
[45] May 13, 1980

[54] ELECTROCARDIOGRAPH ELECTRODES AND ASSOCIATED ASSEMBLIES

[76] Inventors: Harold Mills, 1049 Hillcrest Rd., Beverly Hills, Calif. 90210; Herbert Stein, 238 S. McCarty Dr., Beverly Hills, Calif. 90212

[21] Appl. No.: 816,643

[22] Filed: Jul. 18, 1977

Related U.S. Application Data

[63] Continuation-in-part of Ser. No. 729,797, Oct. 5, 1976, Pat. No. 4,121,575.

[51] Int. Cl.² .............................................. A61B 5/04
[52] U.S. Cl. .................................................... 128/644
[58] Field of Search ............. 128/2.06 E, 2.1 E, 404, 128/410, 411, 416, 417, 418, 380, DIG. 4, 639–642, 643, 644, 783, 791–793, 798, 802, 803

[56] References Cited

U.S. PATENT DOCUMENTS

| 2,433,233 | 12/1947 | Meminger | 128/380 |
| 2,895,479 | 7/1959 | Lloyd | 128/417 |
| 3,409,007 | 11/1968 | Fuller | 128/418 |
| 3,498,291 | 3/1970 | Bunn | 128/2.06 E |
| 3,599,629 | 8/1971 | Gordy | 128/2.06 E |
| 3,788,317 | 1/1974 | McCormick | 128/2.06 E |
| 3,967,628 | 7/1976 | Vredenbregt | 128/417 |
| 3,988,213 | 12/1976 | Price | 128/2.1 E X |
| 4,033,333 | 7/1977 | DeSalvo et al. | 128/2.06 E |

FOREIGN PATENT DOCUMENTS

| 6700019 | 7/1968 | Netherlands | 128/2.06 E |
| 274612 | 4/1951 | Switzerland | 128/DIG. 4 |

OTHER PUBLICATIONS

Barr, et al., "A Device for Rapid ECG Monitoring", Anaesthesia, vol. 27, No. 1, Jan. 1972, pp. 94–96.

*Primary Examiner*—Lee S. Cohen
*Attorney, Agent, or Firm*—L. Lawton Rogers, III

[57] ABSTRACT

An electrocardiograph electrode assembly is disclosed which includes a stretchable elastic strip having apertures in which electrodes are detachably mounted. The electrodes may be six in number and have a proportional spacing with respect to each other corresponding to the average proportional spacing of desired positions on the chest for electrocardiograph monitoring. A holder or retainer is provided for releasably engaging ends of the elastic strip to position and maintain the electrodes in contact with the chest of the patient. The holder may include a system of belts buckled to the strip and threaded through a base member positioned beneath the chest of the patient. Alternatively, weights may be attached to the ends of the strip to maintain the electrodes in contact with the patient's chest without placing a holder or retainer behind the patient.

26 Claims, 19 Drawing Figures

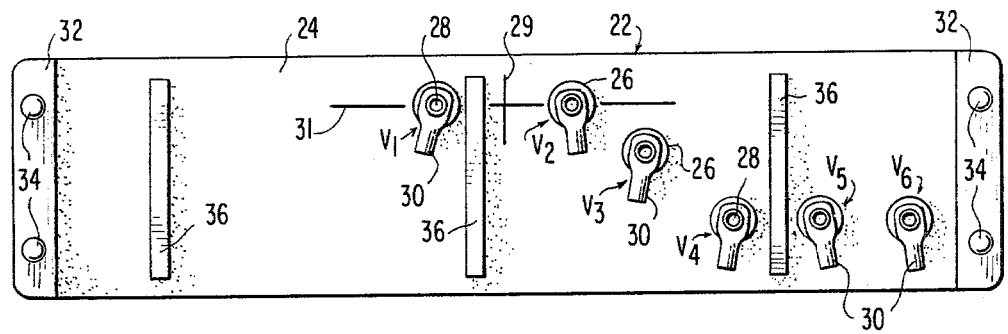
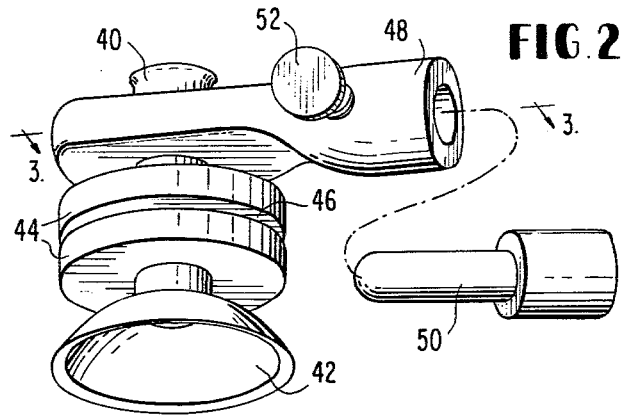
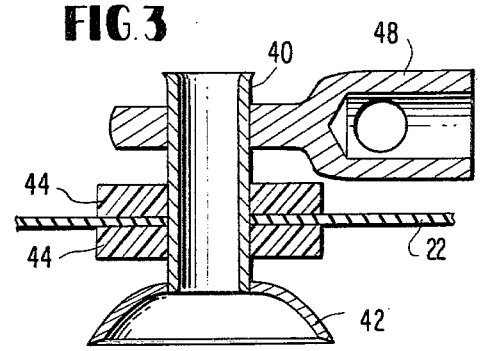
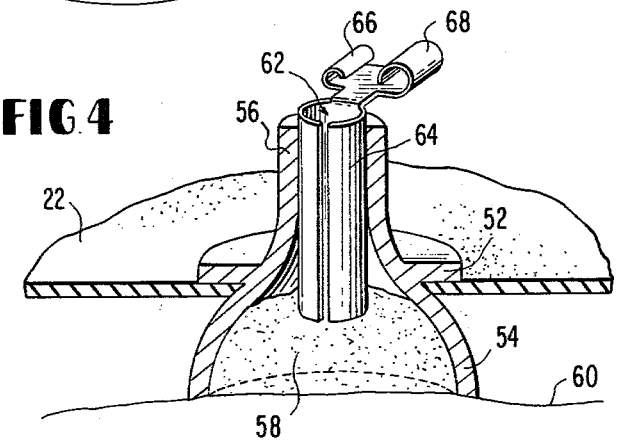
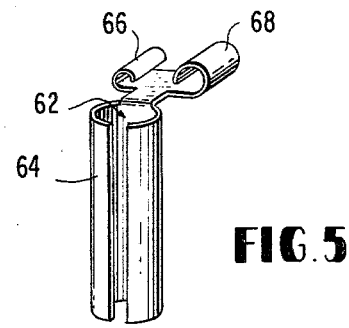
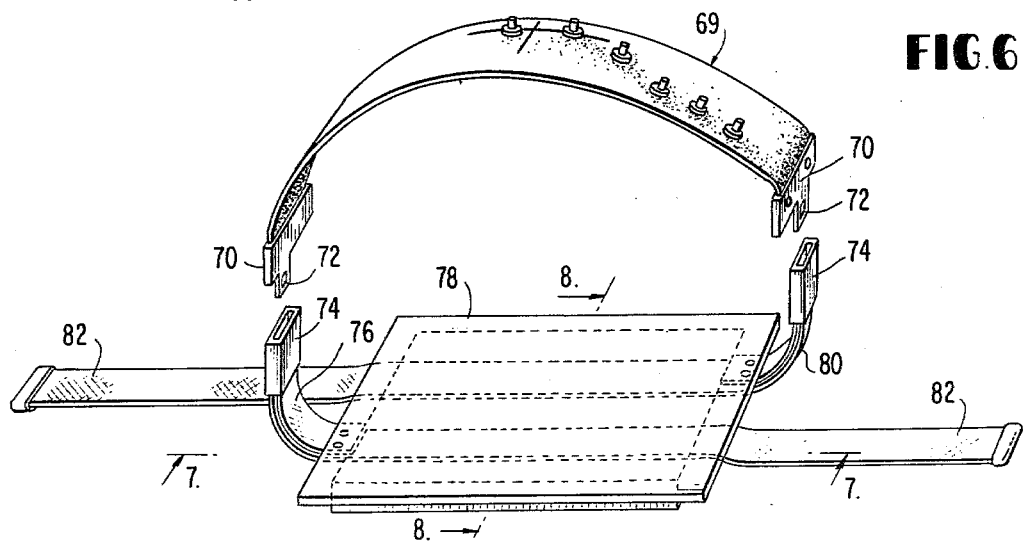

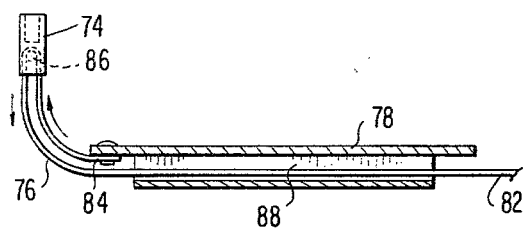
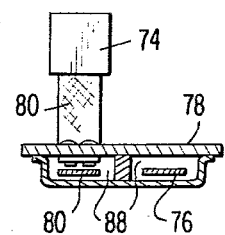
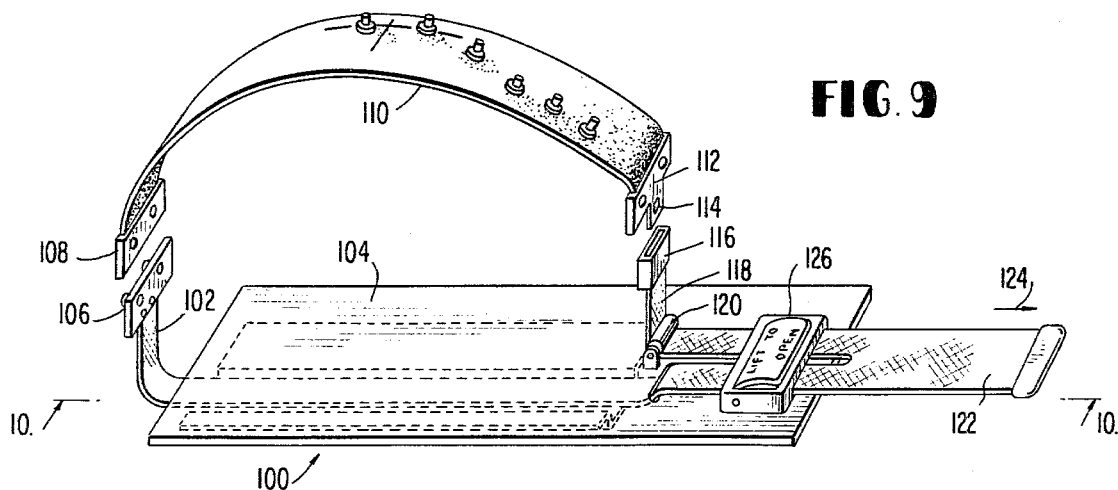
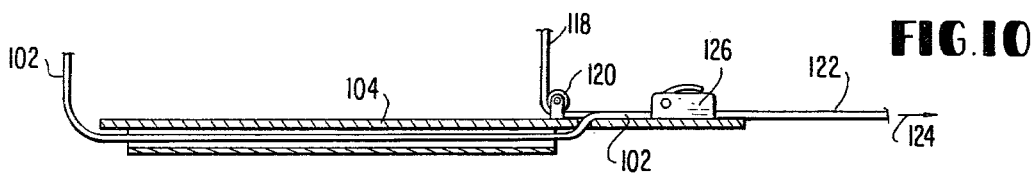
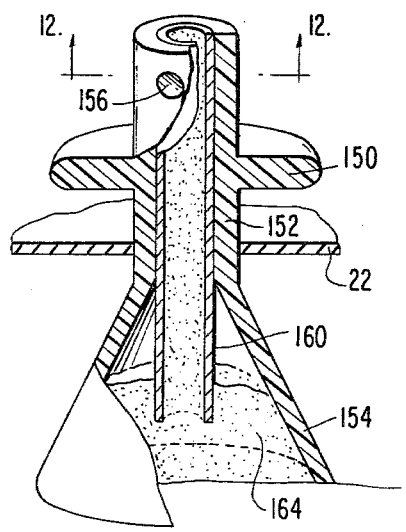
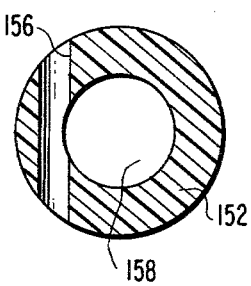
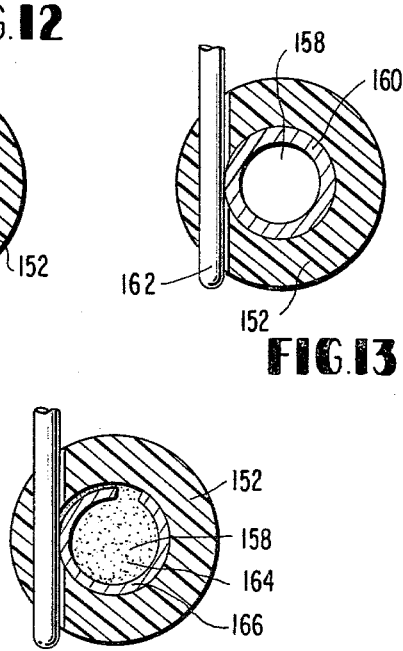

ELECTROCARDIOGRAPH ELECTRODES AND ASSOCIATED ASSEMBLIES

RELATED APPLICATIONS

This application is a continuation-in-part of U.S. application Ser. No. 729,797, filed Oct. 5, 1976, now U.S. Pat. No. 4,121,575, issued Oct. 24, 1978, which is hereby incorporated by reference.

BACKGROUND OF THE INVENTION AND SUMMARY OF PREFERRED EMBODIMENTS

The electrocardiogram (ECG) has proven over the years to be the single most effective clinical record for the diagnosis of cardiac muscle and cardiac nervous conduction abnormalities. An electrocardiogram is routinely taken not only on patients suspected of having cardiac disease, but also on normal patients to establish base line cardiac data. Thus, millions of ECG tracings are recorded yearly in private physicians' offices and in hospitals. It is imperative that these tracings be reliable and also that they be obtained rapidly to minimize the cost. It is to these objectives that the present invention is directed.

Generally, the ECG is usually comprised of twelve distinct records (i.e., tracings) which are obtained from a combination of specific electrical signals obtained from the body of the patient. These signals result from the heart's electrical activity which is conducted throughout the body. The signals, ordinarily in the millivolt range, may be sensed by metal electrodes making electrical contact with the body by way of electrically conductive electrode paste. The signals are transmitted from the electrodes through cables to an electrocardiograph or ECG recorder which includes amplifying circuitry, a heat stylus writing mechanism and switching circuitry. The latter circuitry permits combining the signals ordinarily taken from ten different positions on a patient's body to obtain the twelve tracings ordinarily desired. The twelve tracings, ordinarily adequate to obtain the heart's full spectrum of electrical data, are obtained from electrodes placed on the patient's four extremities and six electrodes carefully positioned on the precordium (i.e. the chest wall of the heart area). The latter six electrodes in the precordial positions are designated as $V_1$, $V_2$, $V_3$, $V_4$, $V_5$ and $V_6$. In certain cases, other positions on the chest may be chosen (e.g. $V_3R$) so that the specific example using positions $V_1$ to $V_6$ is illustrative rather than limiting.

The usual practice is to apply the electrodes to the arms (LA, RA), legs (LL, RL) and precordium ($V_1$, $V_2$, $V_3$, $V_4$, $V_5$ and $V_6$), with the electrodes being of a clamp type, sucton cup type or adhesive type. Such electrodes must be applied one-at-a-time and, in the case of the precordial electrodes particularly, require careful placing at specific anatomical locations. Thus, the careful and time-consuming attention of a skilled nurse, technician or doctor is required.

In a preferred embodiment of the present invention, a chest piece includes a strip of stretchable material, with apertures therein for receiving electrodes. When inserted in the apertures, the spacing between the electrodes and the pattern thereof correspond to the relative proportional spacing of precordial anatomic positions preferred for electrocardiograph monitoring.

Advantageously, each electrode may be provided with flange portions for releasably gripping edges of the apertures, whereby the strip or some or all of the electrodes may be replaced without replacement of the entire chest piece.

Each electrode may include a cup shaped member for containing electrolyte to be placed against the chest of the patient. Advantageously, the electrolyte may be introduced into the cup shaped member through the upper end of a tubular member. The tubular member may carry a terminal for electrical connection to the electrocardiograph machine. The terminal may be rotatable to facilitate electrical contact upon replacement of an electrode since the electrode has no preferred orientation when located in the stretchable strip.

The electrocardiograph electrode assembly may also include a retainer or holder means for engaging the ends of the stretchable strip and for stretching the strip a selectable amount to position and maintain the electrodes in contact witn precordial anatomic positions on the chest of the patient. Advantageously, the holder may be releasably attached to strip end members of the chest piece, which are themselves detachably coupled to the stretchable strips. For example, the holder may include a buckle adapted to engage a buckle catch formed in a strip end member of the chest piece. The strip end member may be detachably coupled to an end of the stretchable strip by snap fasteners thereby facilitating replacement of the stretchable strips without discarding of the strip end member and the associated buckle catch.

In one embodiment, the holder may include a pair of belts adapted for releasable attachment to opposite ends of the stretchable strip. At least one of the belts may be threaded through a base member located behind the patient. By pulling the belts, the chest piece may be quickly and easily stretched to properly position the electrodes and insure that the electrodes make sufficient tight contact with the patient's chest.

In another embodiment, the retainer may take the form of one or more weights for exerting a downward force on ends of the stretchable strip along the sides of the patient's chest. Such an arrangement is particularly suited to monitoring patients lying on a horizontal surface by permitting employment of the electrode assembly without the necessity of placing a holder or retainer behind the patient.

In still another embodiment, the retainer may overlie the chest of the patient and thus obviate the necessity of moving the patient.

It is accordingly an object of the present invention to provide novel and improved method and apparatus for rapidly applying electrocardiograph electrodes to a patient's body in clinically acceptable anatomic regions.

Another object of the invention is to provide novel and improved method and means for applying the precordial electrodes simultaneously and in clinically acceptable anatomic areas on the patient's chest despite a wide range of chest sizes and configurations.

A further object of the invention is to provide novel and improved method and means for applying precordial electrodes in clinical acceptable positions on a patient's chest while facilitating the connection of the leads to the electrocardiograph equipment.

Still another object of the present invention is to provide a novel stretchable chest piece adapted for positioning electrodes.

Yet still another object of the present invention is to provide a novel electrode for electrocardiograph monitoring.

Yet a further object of the present invention is to provide a novel method and apparatus for stretching the chest piece of the present invention across the chest of a patient without the necessity for moving the patient to place a holding means behind him.

These and other objects of the present invention will become apparent from the claims and from the following description when read in conjunction with the appended drawings.

THE DRAWINGS

FIG. 1 is a plan view of a chest piece for establishing anatomically acceptable precordial electrode positions for connection to an electrocardiograph apparatus;

FIG. 2 is a pictorial view of one embodiment of the electrode of the present invention;

FIG. 3 is a cross-sectional view of the electrode of FIG. 2 taken along line 3—3;

FIG. 4 is a pictorial view in partial section of a second embodiment of the electrode of the present invention;

FIG. 5 is a pictorial view of the electrical connector of FIG. 4;

FIG. 6 is a pictorial view of a first embodiment of the electrocardiograph electrode assembly of the present invention, FIG. 7 is a cross-sectional view of the embodiment of FIG. 6 taken along line 7—7;

FIG. 8 is a cross-sectional view of the embodiment of FIG. 6 taken along line 8—8;

FIG. 9 is a pictorial view of a second embodiment of the electrocardiograph electrode assembly of the present invention;

FIG. 10 is a cross-sectional view of the embodiment of FIG. 9 taken along line 10—10;

FIG. 11 is an elevation in partial section of a third embodiment of an electrocardiograph electrode assembly;

FIG. 12 is a cross-section of the embodiment of FIG. 11 taken along line 12—12;

FIG. 13 is the cross-section of FIG. 12 with a sleeve and pin type connector in place therein;

FIG. 14 is the cross-section of FIG. 12 showing the operation of a split sleeve and pin type connector;

DETAILED DESCRIPTION

Figure 15:
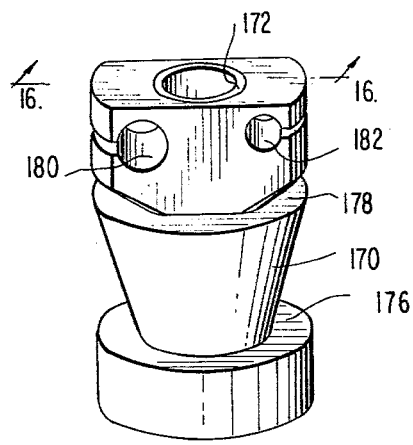
FIG. 15 is a pictorial view of a fourth electrocardiograph electrode assembly.

As illustrated in FIG. 1, a chest piece 22 may comprise a strip 24 of expandable or stretchable material such as rubber sheeting. Extending through the strip 24 are six spaced electrodes 26 designated $V_1$, $V_2$, $V_3$, $V_4$, $V_5$ and $V_6$ in accordance with their positions. The electrodes will be described in greater detail in connection with FIGS. 2 and 3. The electrodes are adapted to receive an electrolyte through apertures 28, which, when the chest piece is disposed on the patient, open outwardly from the chest of the patient. Terminal members 30, which may be rotatably mounted to the electrode, are adapted to receive a cable plug from the electrocardiograph machine.

A significant feature of the construction thus far described is the disposition or location of the electrodes $V_1$ to $V_6$ on the chest of the patient. With the strip 24 of the chest piece in an unstretched condition, these electrodes are spaced suitably for engagement with the correct anatomic contact areas for the precordial electrodes usually designated $V_1$, $V_2$, $V_3$, $V_4$, $V_5$ and $V_6$ on a chest of small size such as that of a ten year old child. To facilitate positioning on the patient, the strip of the chest piece may be provided with a vertical line or mark 29 indicating the location for the mid-chest or mid-sternum line and a horizontal mark 31 indicating the location of the mid-nipple line, i.e. the fourth intercostal space.

With the basic pattern for the electrodes based on the measurements of a small chest as stated, the electrodes can be made to automatically assume the correct anatomic location on a larger chest by stretching the stretchable strip 24 the appropriate amount in securing it to the patient. This is accomplished by employing the holders or retainers described below.

As shown in FIG. 1, the chest piece 22 may include strip end members 32. Advantageously, the strip and members 32 may be detachably coupled to the stretchable strip 24 by means of snap fasteners 34. The strip end members may carry, for example a buckle catch (not shown) or similar device for releasably engaging the holders or retainers hereinafter described. Since both the strip end members and electrodes are readily detachable from the stretchable strip, some or all of the electrodes, and the strips end members can be replaced permitting the remaining components to be reused.

With continued reference to FIG. 1, the strip 22 may include a number of "stays" 36 similar to collar stays. These stays are useful in reducing the reduction in the width of the strip as it is stretched lengthwise across the chest of a patient. They may be attached by any suitable conventional means such as pressure sensitive adhesive.

Referring now to FIGS. 2 and 3 where the electrode 26 of FIG. 1 is illustrated in greater detail, the electrode may include a hollow tubular member 40 made of electrically conductive material and terminate in circular bell-shaped flange portions 42. A pair of circular flanges 44 carried by the tubular member 40 may together form an annular slot 46 configured and dimensioned to engage the edge portions of an aperture in the sheeting material 22 to releasably maintain the electrode 26.

A terminal 48 may be rotatably mounted on the tubular member 40 and may be configured and dimensioned to receive and frictionally engage a banana cable plug 50 connected to an input terminal of a conventional electrocardiograph machine. A thumb screw 52 may be provided to insure an electrical connection with any electrical lead from an electrocardiograph machine.

In operation, the bell or cup shaped portion 42 may be held against the chest of a patient by the stretch of the sheet 22 across the chest of the patient. An electrolyte paste may then be inserted through the top of the tubular member 40 to contact the chest of the patient and thereby provide a low resistance path for the travel of electrical signals between the chest of the patient and the lead of the electrocardiograph machine. The terminal 48 may, if rotatable, be positioned to any convenient orientation and may include a spring biased alligator clip or other suitable electrical connecting means in lieu of the aperture and thumb screw illustrated.

An alternate to the electrode 26 of FIGS. 2 and 3 is illustrated in FIGS. 4 and 5 where the electrode is maintained in place in an aperature in the sheet 22 by a single flange 52 and the bell or cup shaped terminator 54 of the tubular member 56. The electrical connection to the lead of an electrocardiograph machine may be made by means of the electrolyte 58 inserted into contact with the skin 60 of the patient through the central aperature 62 of an electrically conductive connector 64 illustrated in greater detail in FIG. 5.

As shown in FIG. 5, the connector 64 may be a flat metal sheet rolled at one end to form a split sleeve for insertion into the tubular member 56 to be there retained by the spring action of the sleeve. The other end of the connector 64 may be formed into two split sleeves 66 and 68 of different diameters to facilitate the insertion of banana plugs of different sizes.

A holder for a chest piece such as that described in connection with FIG. 1 is illustrated in FIG. 6. With reference to FIG. 6, the chest piece 69 may include strip end members 70, formed with buckle catches 72 for insertion into their respective buckle members 74 to thereby engage the ends of the chest piece 69 with the holder 68.

The holder 68 may include a first belt 76 threaded in a first direction through a base member 78, and a second belt 80 threaded in the opposite direction through the base member 78. As previously noted, one end of each belt may be equipped with a buckle member 74 and the opposite ends 82 of the belts extend from the base member 78 to facilitate grasping and pulling thereof.

Advantageously, the buckle members 74 and belts 80 and 82 may be attached to the base member 78 in the manner depicted in FIG. 7, where one end 84 of the belt may be anchored to the base member 78. The belt may then be disposed about a roller 86 within the buckle member 74 and be threaded through an elongated channel 88 in the base member. In order to tighten the chest piece 69, the end 82 of the belt may be pulled to draw the buckle member 74 toward the anchored belt end 84. When the chest piece is sufficiently stretched, pulling on the end 82 may stop, the buckle member 74 being maintained in position vis-a-vis the belt by frictional engagement between the buckle member, the belt, and the roller 86.

The respective positions of the belts 80 and 82 within the base member are shown in FIG. 8. As shown in FIG. 8, clearance may be provided to permit easy movement of the belts 80 and 82 through the elongated channels 88 of the base member 78. In one embodiment of the present invention, the base member 78 may be formed of rigid or semi-rigid material to resist crushing of the elongated apertures 88 in the base member 78 which might otherwise bind the belts 80 and 82 and inhibit free manipulation of the belts to stretch the chest piece 69.

Referring now to FIGS. 9 and 10, a second embodiment for the chest piece of FIG. 1 is shown. The holder 100 may include a first belt 102 threaded through a channel in base member 104. One end of the belt 102 may be provided with a snap coupling 106 adapted for releasably engaging the strip end piece 108 of the chest piece 110. A second strip end piece 112 of the chest piece 110 may be formed with a buckle catch 114. The buckle catch may be releasably engaged by the buckle member 116 carried by a second belt 118. The secind belt may engage a roller 120 which redirects the second belt 118 so that a portion thereof is nearly parallel to a portion of the first belt 102. The ends of the first and second belts may be joined to facilitate stretching of the chest piece across the chest of the patient.

In operation, the holder 100 may be disposed behind the patient prior to electrocardiograph monitoring. The strip end member 108 may be engaged to the snap fastener 106 of the belt 102. The chest piece 110 may be placed about the chest of the patient and loosely secured in position by buckling the buckle catch 114 with the buckle member 116. The electrodes may be positioned and maintained in contact with the precordial anatomic positions on the chest by pulling on the joined ends of the belts 102 and 118 in the direction of the arrow 124. A quick release seat belt type locking mechanism 126 may be provided to permit movement of the belts 102 and 118 only in the approximate direction of the arrow 124. However, the belts may be quickly released to permit movement in the reverse direction by actuation of the locking mechanism 126.

Figure 17:
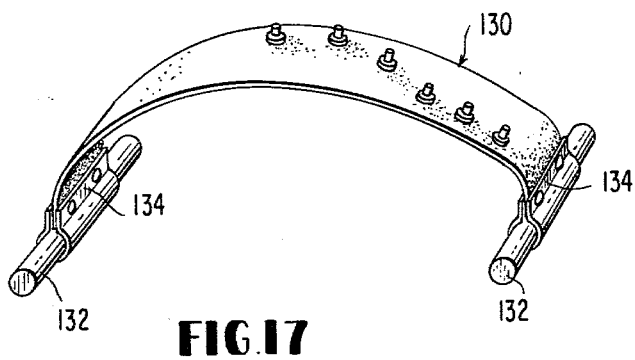
FIG. 17 is a pictorial view of a third embodiment of an electrocardiograph electrode assembly.

FIG. 17 is a pictorial view of the electrocardiograph electrode assembly including means for applying a downward force to ends of an elastic chest piece such as that described in connection with FIG. 1.

A third embodiment of an electrode is illustrated in FIG. 11 where the body of the electrode is provided with a single generally circular flange 150 radially outwardly extending from tubular upper portion 152. A cup shaped lower portion 154 cooperates with the flange 150 to prevent the slippage of the electrode from the stretchable strip 32.

The body of the electrode may be of non-conducting material which is desirably resilient to a minor degree. The upper portion is also provided with one or more lateral bores 156 having a portion common with the axial bore 158 as it illustrated more clearly in FIGS. 12–14.

As shown in FIG. 11 and FIG. 13, a sleeve 160 of electrically conductive material may be inserted into the bore 158 of the non-conductive body of the electrode, the sleeve 160 extending from a point along the uppermost lateral bore to a point just above the bottom of the cup shaped portion of the electrode.

As is illustrated in FIG. 13, a lead of an ECG machine may terminate in an elecrically conductive in 162 adapted for insertion into the lateral bore 156 to be removably held in pressural engagement with the sleeve 160 by the physical configuration of the bores 156 and 158 and/or the resiliency of the material of the electrode body.

As shown in FIG. 11, as electrolyte 164 may be inserted into the cup through the sleeve 160 to thereby establish a low impedance electrical connection between the sleeve and the skin of the patient. The electrolyte may also be utilized to enhance the electrical connection between the sleeve and the pin 162 as shown, for example, in FIG. 14 where the sleeve 166 is longitudinally split to permit passage of the electrolyte into contact with the pin 162.

Figure 16:
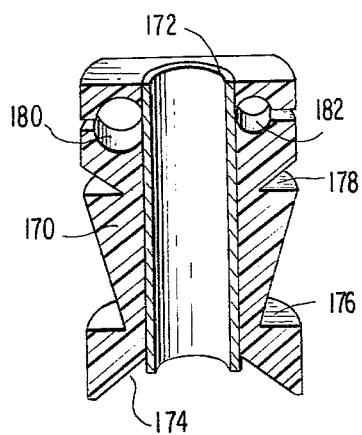
FIG. 16 is a section taken along line 16—16 of FIG. 15.

A fourth embodiment of an electrode is illustrated in FIGS. 15 and 16, where the body 170 is desirably molded out of a plastic material into a generally tubular configuration. As shown in the figures, an electrically conductive thin-walled tube 172 extends substantially the length of the body 170. The lower end of the body is generally in the shape of a truncated cone to form a cavity 174 for electrolyte introduced into the upper end of the tube 172.

The sides of the body 170 are desirably formed to provide notches 176 and 178 at different heights from the bottom of the body. When the present invention is utilized on women with large breasts, greater extension of the electrodes beneath the belt is required for good electrical contact in the $V_2$ and $V_6$ positions. Notch 178 is desirably used in such circumstances.

As also shown in the drawings, two lateral apertures 180 and 182 are provided into which the tube 172 extends. These apertures 180 and 182 are desirably of different sizes to accommodate baynet or banana plugs of differing sizes. The body 170 of the electrode is desirably split into the apertures 180 and 182 to provide a resilient spring action in holding the plug from the electrocardiograph machine into pressural engagement and thus good electrical contact with the tube 172.

It is important to note that the tube 172 may extend upwardly from the top of the body 170 so that a suction cup (not shown) of a conventional type may be attached for use in creating a suctional attachment of the electrode to the patient.

FIG. 17 is a pictorial view of an electrocardiograph electrode assembly including means for applying a downward force to ends of an elastic chest piece such as that described in connection with FIG. 1. The chest piece 130 of FIG. 17 may be stretched to place the electrodes in contact with the proper precordial anatomic positions on the chest of a recining patient by placing the chest piece 130 on the chest of the patient and disposing weights 132 on either side of the patient to exert a downward force on ends 134 of the chest piece thereby stretching the stretchable strip.

Figure 18:
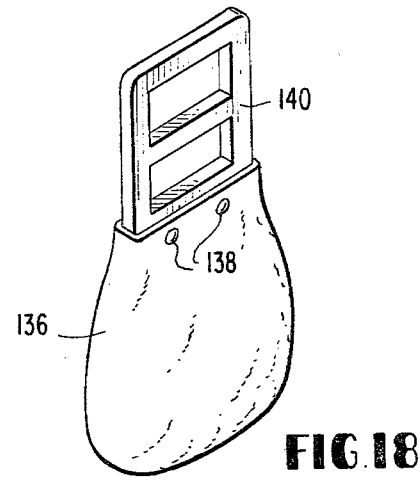
FIG. 18 is a pictorial view of one embodiment of a weight for use in the embodiment of FIG. 17; and, FIG. 19 is a pictorial view of an electrocardiograph electrode assembly with a frame member for overlying the chest of a patient.

The weights may take any desired form but it has been found advantageous for comfort and safety to use a "bean bag" weight such as illustrated in FIG. 18. With reference to FIG. 18, the weight may include a fabric bag 136 of particulate material such as lead pellets or the like connected by any suitable conventional means such as the illustrated fastener 138 to a rigid buckle 140 to which the free ends of the chest piece might be buckled.

Figure 19:
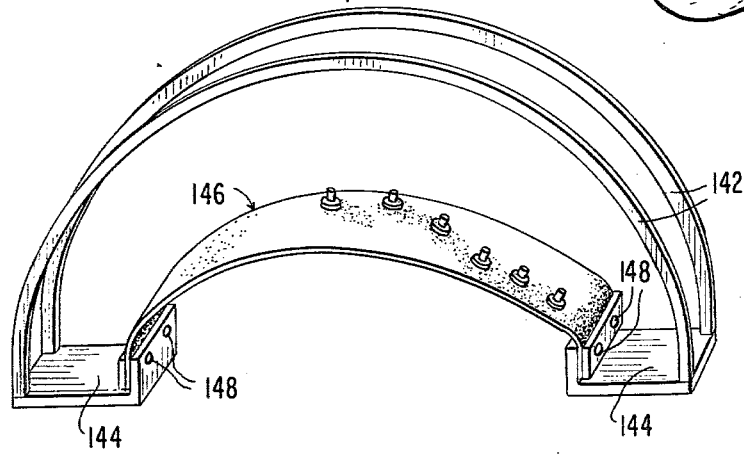

The embodiment of FIG. 17 is particularly desirable where movement of the patient to place some retaining means behind his chest may result in injury or discomfort. Another embodiment not requiring movement of the patient is illustrated in FIG. 19 where the retainer 139 includes arcuate members 142 for bridging the chest of the patient. A surface 144 may be provided on either side of the chest of the patient for receiving weights sufficient to stretch the chest piece 146. The chest piece 146 may be releasably engaged to the retainer 139 by snap fasteners 148.

In operation, the assembly of FIG. 19 may be placed on the chest of a patient lying on a horizontal surface so that the assembly bridges the chest of the patient and so that the chest piece 146 is stretched a sufficient degree to position and maintain the electrodes in contact with the appropriate precordial anatomic positions on the chest of the patient.

The principles, preferred embodiments and modes of operation of the present invention have been described in the foregoing specification. The invention which is intended to be protected is not, however, to be construed as limited to the particular forms disclosed, since these are to be regarded as illustrative rather than restrictive. Variations and changes therefore may be made by those skilled in the art without departing fom the sprit and scope of the present invention.

For example, a chest piece $3\frac{1}{4}''$ wide and 17" long using weights of 2 pounds each which are suitable for adults may be replaced by a chest piece of smaller size and the use of smaller weights for use on infants and the pediatric population.

What is claimed is:

1. An ECG electrode assembly comprising:
   an elongated strip of stretchable nonconductive material having a plurality of apertures arranged in a predetermined pattern with the proportional spacing of the apertures corresponding to the proportional spacing of precordial positions for ECG monitoring;
   means for resisting a reduction in the width of said strip as a result of the elongation of the strip under tension;
   a plurality of electrodes each removably carried by said strip in one of said plurality of apertures, each of said electrodes comprising:
      a hollow member having a portion made of an electrically conductive material, said member being flared at one end to engage the skin of the patient and being open at the other end so that an electrolyte can be inserted into the hollow of said member to establish a low resistance electrical connection between the skin of the patient and the conductive portion of said member;
      a connector means electrically connected to the conductive portion of said member for establishing an electrical connection with the lead of an ECG machine without interfering with the insertion of electrolyte when connected to the lead of an ECG machine; and,
      means carried by said member for removably retaining said electrode in an aperture in said strip;
   means removably attached to each end of said strip for maintaining said strip in position and under tension when manually stretched across the chest of a patient, each of said means comprising a mass of aprticulate material within a flexible container.

2. The ECG electrode assembly of claim 1 wherein said strip is between about two inches and about five inches in width; and,
   wherein said width reduction means includes a plurality of stays spaced along the length of said strip and adhesively secured thereto, each of said stays being disposed across the width of said strip and having a length substantially coextensive with the width thereof.

3. A chest piece for automatically positioning electrocardiograph electrodes on the chest of a patient comprising:
   a strip of stretchable, non-conductive material adapted for positioning on the chest of a patient undergoing electocardiographic monitoring with a predetermined position adjacent each end thereof in a predetermined location relative to the chest of the patient;
   a plurality of electrodes carried by said strip in predetermined locations thereon, each of said electrodes being positioned for contacting a precordial anatomic position of the patient for electrocardiographic monitoring when said strip is positioned in a substantially unstretched condition on the chest of a first patient having a chest of relatively small size; and,
   weight means carried by said strip adjacent opposite ends thereof for stretching said strip to locate said predetermined end positions thereof in said predetermined locations relative to the chest of the patient to thereby increase the spacing between each of said electrodes to position them in the correct precordial anatomic positions for electrocardiographic monitoring on a chest larger in size than the chest of said first patient.

4. The chest piece of claim 3 wherein each of said plurality of electrodes carried by said strip includes:
   a hollow electrically conductive member cup shaped on one end and adapted to receive an electrolyte within the cup to thereby establish a low resistance electrical connection between the electrode and the chest of the patient when the electrode is positioned on the chest of the patient; and,
   retaining means carried by said hollow member for retaining said electrode within an aperture in said strip of stretchable material.

5. The chest piece of claim 4 wherein said retaining means includes a flange extending radially outwardly from the axis of said hollow member, said flange and the cup of said hollow member forming a slot receiving said strip of stretchable material.

6. The chest piece of claim 4 wherein said retaining means includes a pair of flanges extending radially outward from the axis of said hollow member, said flanges forming a slot receiving said strip of stretchable material.

7. The chest piece 1 of claim 1 weherein said weight means includes a pair of weights removably attached one each adjacent the ends of said strip of stretchable material.

8. The chest piece of claim 7 wherein each one of said weights includes particulate material contained within a flexible container.

9. The chest piece of claim 1 wherein said strip of stretchable material includes means for resisting a reduction in the width thereof as said strip is stretched.

10. The chest piece of claim 1 wherein said strip includes selectively removable, non-stretchable end portions removably attached to said weight means.

11. The chest piece of claim 3 wherein each of said electrodes comprises:
   a hollow member of an electrically conductive material, said member being flared at one end to engage the skin of the patient and being open at the other end so that an electrolyte can be inserted into the hollow of said member to establish a low resistance electrical connection between the skin of the patient and said member;
   connector means electrically connected to the other end of said member for establishing an electrical connection with the lead of an ECG machine without interference with the insertion of an electrolyte into the hollow of said member; and
   means carried by said member for removably retaining said electrode in an aperture in said sheet of stretchable material.

12. The chest piece of claim 11 wherein said weight means includes a particulate material within a flexible container attached to said strip adjacent opposite ends thereof.

13. The chest piece of claim 12 including means attached to said strip at a plurality of locations spaced along the length thereof to resist a reduction in width as said strip is longitudinally stretched.

14. The chest piece of claim 13 wherein said connector means includes:
   a first bore generally normal to said hollow member with a portion of said hollow member extending into said first bore,
   said first bore being dimensioned to removably receive a lead from an ECG machine and for retaining the lead in contact with said hollow member to thereby provide a low impedance electrical connection between said hollow member and the lead from the ECG machine; and,
   a second bore generally normal to said hollow member with a portion of said hollow member common to said second bore,
   said second bore being dimensioned to receive a lead from an ECG machine and for retaining the lead in contact with said hollow member to thereby provide a low impedance electrical connection between said hollow member and said lead,
   said first and second bores differing in diameter whereby leads of different diameters may be electrically connected to said electrode.

15. The chest piece of claim 3, wherein each of said electrodes comprises:
   a hollow member flared at one end to engage the skin of the patient and being open at the other end, said member including means for retaining said member in an aperture in said sheet of stretchable material; and
   connector means carried by said hollow member, said connector means having a first portion exposed by said hollow member and a second portion extending into the hollow of said member, said connector means being electrically conductive, and said first portion being adapted for connection to a lead of an ECG machine and said connector means being configured so as to permit the introduction of an electrolyte into the hollow of said member and into contact with said connector means and the skin of the patient while connected to a lead of an ECG machine.

16. The chest piece of claim 15 wherein the hollow member of each of said electrodes is configured to resiliently receive the lead of an ECG machine and for maintaining it in pressural contact with the first portion of said connector means.

17. An ECG electrode comprising:
   a non-metallic member having an upper generally tubular portion and a lower generally cup shaped portion adapted to engage the skin of a patient to thereby form a cavity bounded in part by the skin of the patient for containing an electrolyte,
   said upper portion having a first bore extending from the upper surface of said member downwardly into said cavity,
   said upper portion having a second bore generally normal to said first bore with a portion thereof being common to said first bore; and,
   an electrically conductive generally tubular member disposed in said first bore and a portion of said second bore common thereto and extending downwardly into said cavity whereby electrolyte introduced into said cavity through said conductive member provides a low impedance electrical connection between said conductive member and the skin of the patient,
   said second bore being dimensioned to removably receive a lead from an ECG machine and for retaining the lead in contact with said conductive member to thereby provide a low impedance electrical connection between said conductive member and the lead from the ECG machine.

18. The electrode of claim 17 wherein the upper portion of said non-metallic member includes a third bore generally normal to said first bore with a portion thereof common to said first bore,
- said electrically conductive member being also disposed in a portion of said third bore common to said first bore,
- said third bore being dimensioned to receive a lead from an ECG machine and for retaining the lead in contact with said conductive member to thereby provide a low impedance electrical connection between said conductive member and lead,
- said second and third bore differing in diameter whereby leads of different diameters may be electrically connected to said electrode.

19. A method of applying ECG electrodes to the chest of a patient comprising the steps of:
(a) providing a strip of stretchable non-conductive material having a plurality of apertures arranged in a predetermined pattern with the proportional spacing of the apertures corresponding to the proportional spacing of precordial positions for ECG monitoring;
(b) inserting a hollow electrode into each of the apertures;
(c) attaching a weight to both ends of the strip;
(d) stretching the strip across the chest of the patient with a predetermined point of the strip in a predetermined anatomical position on the chest of the patient;
(e) positioning the weights alongside the chest of the patient to retain the strip in its stretched position;
(f) connecting a lead from an ECG machine to each of the electrodes; and,
(g) applying an electrolyte to the hollow of each electrode in place on the chest of the patient to thereby establish a low impedance connection from the chest of the patient to the ECG machine.

20. A method of automatically positioning electrocardiograph electrodes on the chest of patients of significantly different chest sizes in anatomic precordial locations comprising the steps of:
providing a stretchable chest piece having a plurality of electrodes positioned with respect to each other when the chest piece is unstretched and centered on the chest of a patient of relatively small size to conform to the anatomic precordial locations on the chest of the patient;
stretching the chest piece across the chest of a patient of a relatively large size to place a predetermined position adjacent each end thereof in a predetermined relationship with respect to the chest of the patient while maintaining the chest piece centered with respect to the patient's chest so that the stretching of the chest piece increases the distance between the electrodes and automatically positions the electrodes in the anatomic precordial locations on the chest of the patient with a larger chest size; and,
maintaining the chest piece in its stretched condition across the patient's chest by weights attached to the chest piece adjacent the ends thereof.

21. The method of claim 20 wherein each of the electrocardiograph electrodes includes a passage extending through the chest piece and including the further steps of establishing a low impedance electrical connection between each of the electrodes and the chest of the patient by applying an electrolyte to the passage of each of the electrodes at the end thereof on the side of the chest piece away from the patient's chest.

22. The method of claim 20 wherein the chest piece is maintained in its stretched condition by particulate material in a flexible container.

23. The method of claim 22 wherein each of the electrodes includes a housing having a hollow member flared at one end to engage the skin of the patient and open at the other end so that an electrolyte can be inserted into the hollow to establish a low impedance electrical connection between the skin of the patient and the electrode; and,
including the further step of establishing electrical contact between the lead of an ECG machine and the hollow member by pressural engagement between the lead and a portion of the hollow member external of the hollow.

24. A method of atomatically determining the anatomic precordial location on the chest of patients having significantly different chest sizes comprising the steps of:
providing a chest piece of stretchable material having at least two predetermined positions identifiable as corresponding to a like number of predetemined locations on chests of significantly differing sizes, and carrying indicia of a plurality of anatomical precordial positions;
stretching the chest piece to position the predetermined positions of the chest piece on the corresponding locations on the chest of the patient;
maintaining the chest piece in the stretched condition by means of weights attached to the chest piece adjacent opposite ends thereof; and
determining a plurality of anatomical precordial locations on the chest of the patient by reference to the indicia carried by the chest piece.

25. Apparatus for automatically locating a plurality of anatomic precordial locations on the chests of patients of significantly different chest sizes comprising:
a strip of non-conductive stretchable material adapted for positioning on the chest of a patient; and,
a weight attached to said strip adjacent each end thereof,
said strip having means for identifying at least two predetermined positions thereon corresponding to like numbered locations of the chest of a patient,
said strip having a longitudinal dimension sufficient to permit positioning of said at least two identified predetermined positions on the correspondng locations on the chest of a patient of relatively small size with the strip in a substantially unstretched condition but insufficient to permit positioning of said at least two predetemined positions on the corresponding locations on the chest of a patient of relatively large size with the strip in said substantially unstretched condition,
said strip having a plurality of apertures in predetermined positions with respect to each other and to said at least two predetermined positions with said strip in an unstretched condition,
said strip being stretchable in a longitudinal direction sufficiently to position said at least two identified predetermined positions on corresponding locations on the chest of a patient of relatively large size, the stretchable nature of the strip allowing the spacing between adjacent ones of said plurality of apertures to vary as a function of the stretching of said strip so that the position of said plurality of apertures locates the anatomic precordial positions on the chest of the patient of relatively large size on which said strip is positioned.

26. A method of placing a plurality of ECG electrodes on the chest of a patient comprising the steps of:
   (a) supporting the patient in the supine position;
   (b) providing a stretchable chest piece having a weight secured thereto adjacent opposite ends thereof and a plurality of electrodes positioned with respect to each other when the chest piece is unstretched and centered on the chest of a patient of relatively small size to conform to the anatomic precordial locations on the chest of the patient, each of the electrocardiograph electrodes including a passage extending through the chest piece and at least one of the electrocardiograph electrodes being electrically connected to the lead of an ECG machine;
   (c) maintaining the chest piece in a stretched condition across the chest of a patient of a relative large size by positioning one of the weights on the support for the patient adjacent the chest of the patient on each side thereof while maintaining the chest piece centered with respect to the patient's chest so that the stretching of the chest piece increases the distance between the electrodes and automatically positions the electrodes in the anatomic precordial locations on the chest of the patient with a larger chest size; and,
   (d) establishijng a low impedance electrical connection between each of the electrodes and the chest of the patient by applying an electrolyte to the end of the passage of each of the electrodes on the side of the chest piece away from the patient's chest.

* * * * *